(12) United States Patent
Winner et al.

(10) Patent No.: US 10,750,692 B2
(45) Date of Patent: Aug. 25, 2020

(54) **ALTERED PIGMENT DEPOSITION IN *TAGETES PATULA***

(71) Applicant: Ball Horticultural Company, West Chicago, IL (US)

(72) Inventors: Blair L. Winner, Ventura, CA (US); Jayaraj Alappat, Aurora, IL (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 1043 days.

(21) Appl. No.: 14/931,601

(22) Filed: Nov. 3, 2015

(65) Prior Publication Data

US 2016/0122773 A1 May 5, 2016

Related U.S. Application Data

(60) Provisional application No. 62/075,205, filed on Nov. 4, 2014.

(51) Int. Cl.
*A01H 6/14* (2018.01)
*A01H 5/02* (2018.01)

(52) U.S. Cl.
CPC ............... *A01H 5/02* (2013.01); *A01H 6/14* (2018.05)

(58) Field of Classification Search
CPC ........................................................ A01H 6/14
See application file for complete search history.

(56) References Cited

U.S. PATENT DOCUMENTS

| 6,784,351 B2 | 8/2004 | Hauptmann |
| 2010/0021962 A1 | 1/2010 | Sauer et al. |
| 2011/0023162 A1 | 1/2011 | Brugliera et al. |
| 2011/0247092 A1 | 10/2011 | Dohm et al. |
| 2013/0145491 A1 | 6/2013 | Shields et al. |

FOREIGN PATENT DOCUMENTS

| JP | 2009-034074 | 2/2009 |
| WO | WO 2004/002214 | 1/2004 |

OTHER PUBLICATIONS

Deineka et al 2016, Research Journal of Pharmaceutical, Biological and Chemical Science 7(5): 2986-2993.*
Howe et al 1997, Proc. Fla. State Hort. Soc. 110: 350-357.*
Delgado-Vargas et al., "Natural pigments: carotenoids, anthocyanins, and betalains—characteristics, biosynthesis, processing, and stability," *Crit. Rev. Food Sci. Nutri.*, 40(3):173-289, 2000.
Winkel-Sirley, "Flavonoid Biosynthesis: A Colorful Model for Genetics, Biochemistry, Cell Biology, and Biotechnology," *Plant Physiology*, 126:485-493, 2001.
Wu et al., "Concentrations of anthocyanins in common foods in the United States and estimation of normal consumption," *J. Agric. Food Chem.*, 54(11):4069-4075, 2006.
International Search Report and Written Opinion for International Application No. PCT/US2015/058813, dated Mar. 3, 2016.
European Extended Search Report regarding European Application No. 15856545, dated Mar. 22, 2018.

\* cited by examiner

*Primary Examiner* — David H Kruse
(74) *Attorney, Agent, or Firm* — Dentons US LLP

(57) ABSTRACT

The invention provides *Tagetes patula* ray florets comprising cyanidin-3-rutinoside, cyanidin-3-glucoside, petunidin-3-glucoside, and cyanidin in the lower epidermal layers. The invention also provides *Tagetes* plants comprising a mutant prdr1-1 allele and methods for producing a plant produced by crossing such plants with themselves or with another plant, such as a plant of another genotype. The invention further relates to seeds and plants produced by crossing *Tagetes* plants comprising a mutant prdr1-1 allele. The invention further relates to parts of such plants.

12 Claims, 4 Drawing Sheets

'PAS1146954'

ALTERED PIGMENT DEPOSITION IN *TAGETES PATULA*

CROSS REFERENCE TO RELATED APPLICATIONS

This application claims priority to U.S. Provisional Application No. 62/075,205, filed Nov. 4, 2014, which is herein incorporated by reference in its entirety.

FIELD OF THE INVENTION

The present invention relates to the field of plant breeding and, more specifically, to *Tagetes patula* ray florets comprising anthocyanin pigment in the lower epidermal layers of the ray floret and related methods and compositions for the production thereof.

BACKGROUND OF THE INVENTION

The goal of plant breeding is to combine various desirable traits in a single variety/hybrid. Such desirable traits may include any trait deemed beneficial by a grower and/or consumer, including desirable flower color or pattern, resistance to insects or disease and tolerance to environmental stress.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci.

Conversely, a cross of two plants each heterozygous at a number of loci produces a population of hybrid plants that differ genetically and are not uniform. The resulting non-uniformity makes performance unpredictable.

The *Tagetes* genus is a member of the family Asteraceae, alternatively known as Compositae, and comprises around thirty species of strongly scented annual or perennial herbs. *Tagetes* are native from Arizona and New Mexico to Argentina. Cultivated genera include *Tagetes erecta* commonly referred to as African marigold, *Tagetes patula* or the French marigold, *Tagetes erecta x patula* also known as the triploid marigolds, and *Tagetes tenuifolia* also known as *Tagetes signata* or commonly signet marigold. Of the cultivated marigolds, the French marigolds are especially valued in the landscape as a colorful upright-mounding border plant. Cultivated marigolds perform well in dry or moist conditions with strong-scented, showy flowers that are excellent in borders and as cut flowers. They produce a long-term display of colors, which include yellow, orange, and gold with shades of red and maroon from the triploids and French types. Flowers range in size from 2.5 cm for the French varieties to as broad a 13 cm for some of the African varieties. Plants range from 15 cm in height to 91 cm and fill in well in the garden.

SUMMARY OF THE INVENTION

In one aspect, the invention provides a *Tagetes patula* ray floret comprising cyanidin-3-rutinoside, cyanidin-3-glucoside, petunidin-3-glucoside, and cyanidin in the lower epidermal layers of the ray floret. In one embodiment, the ray floret further comprises a prdr1-1 allele. In another embodiment, the prdr1-1 allele confers a red color in the lower epidermal layers of the ray floret. In other embodiments, the invention provides a plant comprising such a ray floret or a seed that produces such a plant. In still further embodiments, the ray floret may comprise a transgene or a single locus conversion.

In another aspect, the invention provides a *Tagetes patula* plant comprising a prdr1-1 allele that confers to the plant anthocyanin pigment in the lower epidermal layers of the ray floret, wherein a representative deposit of seed comprising said allele has been deposited under ATCC Accession No. PTA-121614. In some embodiments, the plant is homozygous for the allele, or the plant is heterozygous for the allele. In other embodiments, the plant is hybrid, or the plant is inbred. In another embodiment, the anthocyanin pigment confers a red color in the lower epidermal layers of the ray floret. In another embodiment, the anthocyanin conferring the red color is petunidin-3-glucoside. In further embodiments, the plant comprises a transgene, or the plant comprises a single locus conversion. In still further embodiments, the invention provides a plant part comprising a cell of such a plant, such as a cutting, leaf, a floret, an ovule, pollen, or a flower. In another embodiment, the invention provides a seed that produces such a plant. In still other embodiments, the invention provides a tissue culture of regenerable cells of such a plant, for example a tissue culture comprising cells or protoplasts from a plant part selected from the group consisting of embryos, meristems, cotyledons, pollen, leaves, anthers, roots, root tips, pistil, flower, florets, seed, stems, and protoplasts or callus derived therefrom. In a still further embodiment, the invention provides a plant regenerated from such a tissue culture, wherein the regenerated plant comprises the prdr1-1 allele. In other embodiment, the invention provides an F1 hybrid seed having as one parent a *Tagetes patula* plant comprising a prdr1-1 allele that confers to the plant anthocyanin pigment in the lower epidermal layers of the ray floret. In other embodiments, said plant is a male parent, or is a female parent. In further embodiments, the invention provides a plant produced by growing such a seed, wherein the plant comprises the prdr1-1 allele, or a plant part comprising a cell of such a plant, such as a cutting, leaf, a floret, an ovule, pollen, or a flower.

In another aspect, the invention provides a method of introducing a desired trait into a plant comprising: (a) crossing a *Tagetes patula* plant comprising a prdr1-1 allele that confers to the plant anthocyanin pigment in the lower epidermal layers of the ray floret with a second plant that comprises a desired trait to produce F1 progeny; (b) selecting an F1 progeny that comprises the desired trait; (c) crossing the selected F1 progeny with another *Tagetes patula* plant comprising a prdr1-1 allele that confers to the plant anthocyanin pigment in the lower epidermal layers of the ray floret to produce backcross progeny; and (d) repeating steps (c) and (d) three or more times in succession to produce selected fourth or higher backcross progeny that comprise the desired trait. In one embodiment, the invention provides a plant produced by such a method, wherein the plant comprises said prdr1-1 allele. In a further embodiment, the invention provides a method of producing a plant comprising an added desired trait, the method comprising introducing a transgene or single locus conversion conferring the desired trait into a *Tagetes patula* plant comprising a prdr1-1 allele that confers to the plant anthocyanin pigment in the lower epidermal layers of the ray floret, wherein a representative deposit of seed comprising said allele has been deposited under ATCC Accession No. PTA-121614.

In another aspect, the invention provides a method for producing *Tagetes* seed comprising the steps of: (a) crossing a *Tagetes patula* plant comprising a prdr1-1 allele that confers to the plant anthocyanin pigment in the lower epidermal layers of the ray floret with itself or a second plant capable of being crossed thereto; and (b) collecting resulting seed. In one embodiment, the second plant is a *Tagetes erecta* plant. In another embodiment, the method further comprises the steps of: (c) crossing a plant grown from said seed of step (b) with itself or a different plant at least one additional time to yield additional seed. In another embodiment, the plant is a plant of *Tagetes* variety TAS1146954', a sample of seed of said *Tagetes* variety having been deposited under ATCC Accession Number PTA-121614.

In another aspect, the invention provides a method of producing a *Tagetes* plant with a prdr1-1 allele that confers the presence of anthocyanin pigment in the lower epidermal layers of the ray floret, said method comprising introgressing the prdr1-1 allele from a *Tagetes patula* plant comprising a prdr1-1 allele that confers to the plant anthocyanin pigment in the lower epidermal layers of the ray floret into a plant of a different genotype. In an embodiment, said prdr1-1 allele has been inherited from *Tagetes* variety TAS1146954' or a progeny of any generation thereof comprising said allele, a sample of seed comprising the allele having been deposited under ATCC Accession Number PTA-121614.

DETAILED DESCRIPTION OF THE INVENTION

The invention provides *Tagetes patula* ray florets comprising cyanidin-3-rutinoside, cyanidin-3-glucoside, petunidin-3-glucoside, and cyanidin in the lower epidermal layers of the ray floret. The invention also provides *Tagetes* plants and parts thereof comprising a prdr1-1 allele that confers the presence of the anthocyanin pigment petunidin-3-glucoside in the lower epidermal layers of the ray floret. The presence of this pigment in the lower epidermal layers is novel and not found in other varieties of *Tagetes*, thus resulting in *Tagetes* plants with flowers having unique shades of red and previously unobserved speckled patterns. Chemical analysis of the ray florets from plants comprising the mutant prdr1-1 allele and comparison against representatives of all known *Tagetes patula* color type revealed the chemical distinctiveness of these ray florets, in addition to their unique appearance.

Through breeding of plants containing the mutant allele with plants containing both high and low carotenoid concentrations, the inventors were able to produce new *Tagetes* marigold varieties having flowers of novel shades of red and also novel pigmentation patterns. As the trait described herein is believed to be a dominant trait, the amount of pigment may therefore be augmented by crossing of plants of the invention with plants having higher or lower relative levels of flower anthocyanins or carotenoids.

Figure 1:
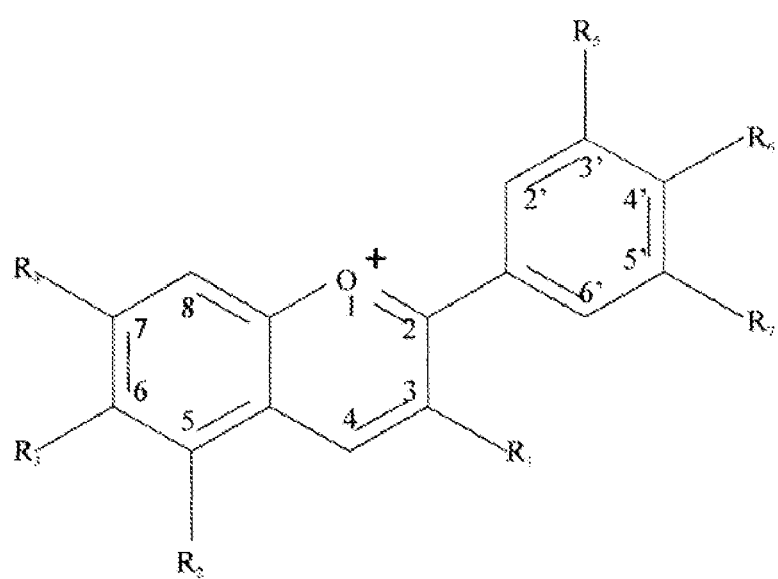
FIG. 1—Shows the basic structure of anthocyanidin pigments. Rx represents —H, —OH, or —OCH3 groups, depending on the pigment considered.
Figure 2:
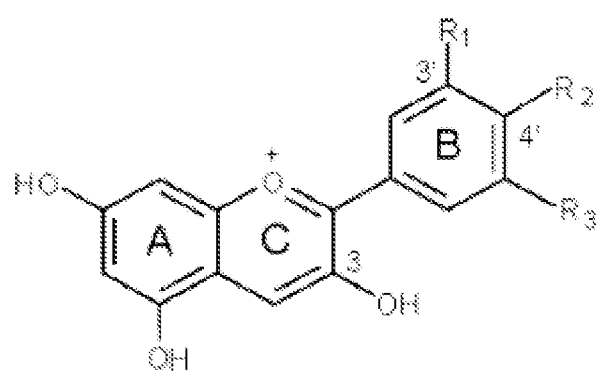
FIG. 2—Shows chemical structures of six naturally occurring common anthocyanidins.

Anthocyanins are water soluble vacuolar pigments found throughout the tissues of vascular plants that confer orange, red, purple, and blue colors to the plant parts in which they accumulate. These compounds play key roles in the recruitment of pollinators and seed dispersers, signaling between plants and microbes, defense as antimicrobial agents, and UV protection (Winkel-Sirley, *Plant Physiology* 126:485-493, 2001). Anthocyanins are derived from anthocyanidins, the aglycone form, by adding sugars to form glycosides and acyl glycosides. The basic structure of anthocyanidins is shown in FIG. 1 (Delgado-Vargas et al., *Crit. Rev. Food Sci. Nutri.* 40:173-289, 2000). FIG. 2 shows chemical structures of six common naturally occurring anthocyanidins, including petunidin (Wu, *J. agric. Food Chem.* 54:4069-4075, 2006). Methods of assaying for anthocyanin content are known in the art.

A. Breeding *Tagetes* Plants Comprising a Prdr1-1 Allele

The development of new varieties using one or more starting varieties is well known in the art and encompassed by the invention. In accordance with the invention, novel varieties may be created by crossing a plant of the invention followed by multiple generations of breeding according to such well-known methods. New varieties may be created by crossing with any second plant.

In selecting a second plant to cross with a plant of the invention, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, flower color or size, color patterning, foliage quality, floret size, shape and uniformity, maturity date, flower yield, seed germination rate, seedling vigor, disease tolerance or resistance, and adaptability for soil and climate conditions. Consumer-driven traits are other traits that may be incorporated into new plants developed by this invention.

One aspect of the current invention therefore provides methods for producing a plant with an anthocyanin pigment in the lower epidermal layers of the ray floret. In certain embodiments, such a method may comprise: (a) crossing a *Tagetes patula* plant comprising a prdr1-1 allele that confers to the plant an anthocyanin pigment in the lower epidermal layers of the ray floret with a second plant that comprise at least a first desired trait to produce F1 progeny; (b) selecting an F1 progeny that comprises the anthocyanin pigment in the lower epidermal layers of the ray floret and desired trait(s); (c) crossing the selected F1 progeny with itself or another *Tagetes* plant; and (d) repeating steps (c) and (d) three or more times in succession to produce selected fourth or higher generation progeny that comprise anthocyanin pigment in the lower epidermal layers of the ray floret and one or more desired trait(s). In a particular embodiment, the second plant may be a *Tagetes patula* plant and the progeny seed may be planted and grown to produce fertile hybrid progeny plants. A plant in accordance with the invention may be used in such crosses as the female plant or the male plant.

The invention also provides methods of producing *Tagetes* comprising (a) crossing a *Tagetes patula* plant comprising a prdr1-1 allele as described herein with itself or a second plant capable of being crossed thereto; and (b) collecting resulting seed. In one embodiment, the second plant may be a *Tagetes erecta* plant. In some embodiments, the methods of the present invention may further comprise the step of (c) crossing a plant grown from said seed of step (b) with itself or a second plant at least one or more additional time(s) to yield additional seed. In another embodiment, the second plant may be a plant of *Tagetes* variety TAS1146954'. Plants, seeds, and plant parts produced from the methods described herein and which comprise a prdr1-1 allele as described herein are also provided.

In certain embodiments, hybrid seeds may be produced using the methods of the present invention. A parent plant of such a seed may be a *Tagetes patula* plant comprising a prdr1-1 allele that confers to the plant an anthocyanin pigment in the lower epidermal layers of the ray floret. In other embodiments, a plant as described herein may be either the male plant or the female plant in a given cross.

In accordance with the invention, any species of *Tagetes* may be used. In particular, *Tagetes* species that may be useful include but are not limited to *Tagetes patula, Tagetes erecta, Tagetes lucida, Tagetes minuta, Tagetes tenuifolia, Tagetes argentina, Tagetes biflora, Tagetes campanulata, Tagetes dianthiflora, Tagetes elliptica, Tagetes, filifolia, Tagetes Foetidissima, Tagetes heterocarpha, Tagetes hartwegii, Tagetes laxa, Tagetes Lemmoni, Tagetes micrantha*, and the like.

In a further embodiment, a *Tagetes patula* plant as described herein may be used as a male parent plant and crossed with a *Tagetes erecta* plant as a female parent plant to obtain triploid (3N) marigold progeny seeds. Such seeds may be planted and grown to produce sterile triploid progeny plants. Such methods as described herein may be used for propagation of a plant comprising an anthocyanin in the lower epidermal layers of the ray floret, or can be used to produce plants that are derived from such a plant. Plants derived from a plant with an anthocyanin in the lower epidermal layers of the ray floret may be used, in certain embodiments, for the development of new varieties of *Tagetes*.

In certain other embodiments, a plant of the invention may be an inbred plant, or may be a hybrid plant. In addition, a plant of the present invention may be homozygous for a prdr1-1 allele that confers to the plant an anthocyanin pigment in the lower epidermal layers of the ray floret or a plant of the invention may be heterozygous for the allele.

In certain embodiments, the present invention provides plants modified using the methods described herein to include at least a first desired heritable trait. Such plants may, in one embodiment, be developed by backcrossing, wherein essentially all of the desired morphological and physiological characteristics of a variety are recovered in addition to a genetic locus transferred into the plant via the backcrossing technique. The term single locus converted plant as used herein refers to those plants which are developed by backcrossing, wherein essentially all of the desired morphological and physiological characteristics of a variety are recovered in addition to the single locus transferred into the variety via the backcrossing technique. By essentially all of the desired morphological and physiological characteristics, it is meant that the characteristics of a plant are recovered that are otherwise present when compared in the same environment, other than an occasional variant trait that might arise during backcrossing or direct introduction of a transgene.

Backcrossing can be used to improve a variety, and may be used, for example, to introduce a prdr1-1 allele into the plant genetic background of any plant that is sexually compatible with *Tagetes patula*, as well as to introduce one or more traits into a plant of the invention. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular non-recurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcros sing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants comprising an anthocyanin pigment in the lower epidermal layers of the ray floret. This technique uses different recurrent parents during the backcrossing. Modified backcrossing may be used to replace the original recurrent parent with a variety having certain more desirable characteristics or multiple parents may be used to obtain different desirable characteristics from each.

B. Further Embodiments of the Invention

In other embodiments, the invention provides methods of vegetatively propagating a *Tagetes* plant of the invention. Such a method may comprise the steps of: comprising the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing *Tagetes* plants from the rooted plantlets. In still further embodiments, a plant of the invention is propagated by seed, wherein a plant comprising a prdr1-1 allele may be used as either a female or a male parent for producing progeny seed and plants.

Also provided are methods of producing a *Tagetes* plant with a prdr1-1 allele that confers the presence of an anthocyanin pigment in the lower epidermal layers of the ray floret, said method comprising introgressing the prdr1-1 allele from a plant comprising such an allele into a plant of a different genotype. In certain embodiments, the prdr1-1 allele may be inherited from *Tagetes* variety TAS1146954' or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of marigold plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

C. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing.

Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunl, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant comprising an anthocyanin pigment in the lower epidermal layers of the ray floret according to the invention. Non-limiting examples of particular genes and corresponding phenotypes one may choose to introduce into a of the invention include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

D. Definitions

In the description and tables herein, a number of terms are used. In order to provide a clear and consistent understanding of the specification and claims, the following definitions are provided:

Aglycon (Aglycone): The non-sugar compound remaining after replacement of the glycosyl group from a glycoside by a hydrogen atom.

Allele: Any of one or more alternative forms of a gene locus, all of which alleles relate to one trait or characteristic. In a diploid cell or organism, the two alleles of a given gene occupy corresponding loci on a pair of homologous chromosomes.

Anthocyanidin: An extended conjugation made up of C6-C3-C6 flavonoid skeleton.

Anthocyanin: Anthocyanins are a group of plant pigments that generally occur in the plant as glycosides and acylglycosides of anthocyanidins, the aglycones. Anthocyanidins vary in the different hydroxyl or methoxyl substitutions in their basic flavylium (2-phenylbenzopyrilium) structure. In accordance with the invention, a *Tagetes* plant as described herein comprises the anthocyanin petunidin-3-glucoside in the lower epidermal layers of the ray floret. In particular, plants of the invention may comprise any percent petunidin-3-glucoside in the lower epidermal layers of the ray floret. For example, such a plant may comprise a percent petunidin-3-glucoside in the lower epidermal layers of the ray floret including, but not limited to about 0.1% to about 3%, including about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, and about 3.0%. In other embodiments, a plant of the invention may comprise a percent petunidin-3-glucoside in the lower epidermal layers of the ray floret including, but not limited to about 3%, about 4%, about 5%, about 6%, about 7%, about 8%, about 9%, about 10%, or more.

Backcrossing: A process in which a breeder repeatedly crosses hybrid progeny, for example a first generation hybrid (F1), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

F1 Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Phenotype: The detectable characteristics of a cell or organism, which characteristics are the manifestation of gene expression.

Plant Part: As used herein, a plant part refers to a part of a plant of the present invention. A plant part may be defined as comprising a cell of such plant, such as a cutting, a leaf, a floret, an ovule, pollen, a cell, a seed, a flower, an embryo, a meristem, a cotyledon, an anther, a root, a root tip, a pistil, a stalk, a stem, and a protoplast or callus derived therefrom.

Quantitative Trait Loci (QTL): Quantitative trait loci (QTL) refer to genetic loci that control to some degree numerically representable traits that are usually continuously distributed.

Regeneration: The development of a plant from tissue culture. In accordance with the invention, a regenerated marigold plant as described herein would comprise the prdr1-1 allele that confers a red pigment in the lower epidermal layers of the ray floret.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a marigold variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant. A tissue culture in accordance with the invention may originate from or comprise cells or protoplasts from a plant part selected from the group consisting of embryos, meristems, cotyledons, pollen, leaves, anthers, roots, root tips, pistil, flower, florets, seed, stems, and protoplasts or callus derived therefrom.

E. Deposit Information

A deposit of at least 2,500 seeds of *Tagetes patula* variety 'PAS 1146954', disclosed above and recited in the claims, has been made with the American Type Culture Collection (ATCC), 10801 University Blvd., Manassas, Va. 20110-2209. The date of the deposit was Sep. 25, 2014. The accession number for those deposited seeds of *Tagetes patula* variety 'PAS 1146954' is ATCC Accession Number PTA-121614. Upon issuance of a patent, all restrictions upon the deposits will be removed, and the deposits are intended to meet all of the requirements of 37 C.F.R. § 1.801-1.809. The deposit[s] has been accepted under the Budapest Treaty and will be maintained in the depository for a period of 30 years, or 5 years after the last request, or for the effective life of the patent, whichever is longer, and will be replaced if necessary during that period.

EXAMPLES

Although the foregoing invention has been described in some detail by way of illustration and example for purposes of clarity and understanding, it will be obvious that certain changes and modifications may be practiced within the scope of the invention, as limited only by the scope of the appended claims.

Example 1

Identification of *Tagetes* Plants with Mutant prdr1-1 Allele

The present invention was discovered in two French marigold plants, *Tagetes patula*, from a selfed population of breeding line 71733F3-2-2-1. The mutant marigold plants were coded 71733F3-2-2-1-1 and 71733F3-2-2-1-2. The mutant allele was designated prdr1-1 and is visually characterized by the presence of a red pigment in the lower epidermal layers of the ray florets. Early crosses with the mutant selections yielded novel red flower colors that were brighter and more intense than any previously known French marigold. The progeny plants of these crosses thus possessed different overall color patterns and different overall shades of red. When plants having the mutant allele were crossed with other French marigolds having different genetic backgrounds, new flower colors and patterns never before observed in French marigold were observed in the progeny. The unique colors developed from this new prdr1-1 mutation include but are not limited to bright red, dark brown red, and patterns including an unexpected speckled pattern.

The mutant plants, 71733F3-2-2-1-1 and 71733F3-2-2-1-2, containing the mutant allele prdr1-1 of the present invention, were self-pollinated and crossed with various breeding lines. Based on hybrid and F2 populations, the presence of a red pigment in the lower epidermal layers of the ray florets was identified in the mutant plants but not in the wild-type plants. This pigment deposition in the lower epidermal layers of the ray florets appears to be a dominant trait, while the amount of pigment is inherited quantitatively.

Example 2

Development of Homozygous Mutant Inbred Lines and Breeding of the Mutant Lines

Mutant plants designated 71733F3-2-2-1-1 and 71733F3-2-2-1-2, containing the mutant allele prdr1-1 of the present invention were self-pollinated and crossed with various breeding lines from at least as early as 1997. After up to 7 generations of self-pollination and selection from 2005 to 2012, over 12 homozygous inbred mutant French marigold lines were produced with unique phenotypes, such as different overall color patterns and different overall shades of red. All of these mutant lines were found to possess a red pigment in the lower epidermal layers of the ray florets.

Figure 3:
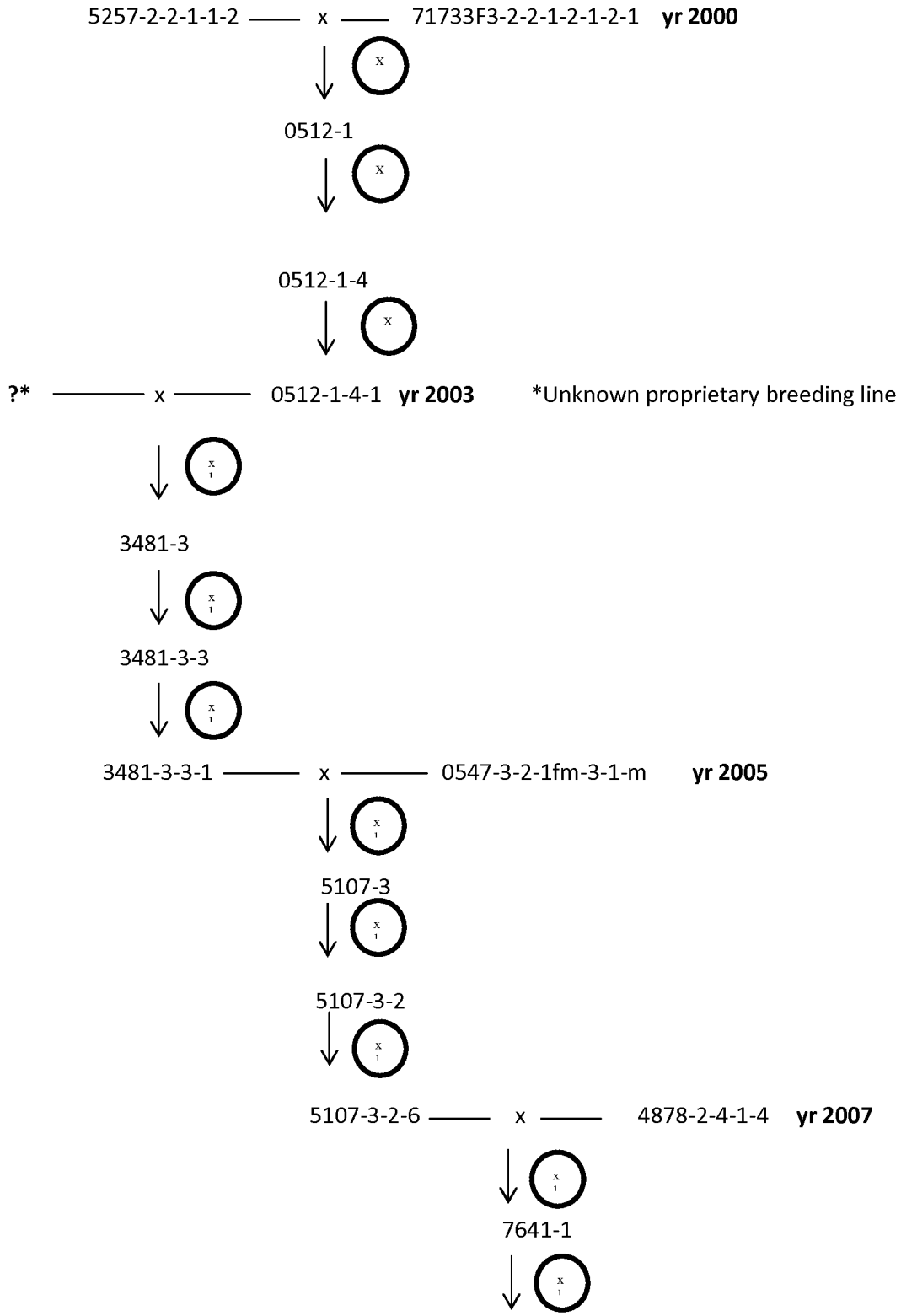
FIG. 3—Shows the origin and breeding history of *Tagetes patula* variety TAS1146954'. TAS1146954' corresponds to MT35423 in Tables 1 and 2.
Figure 3:
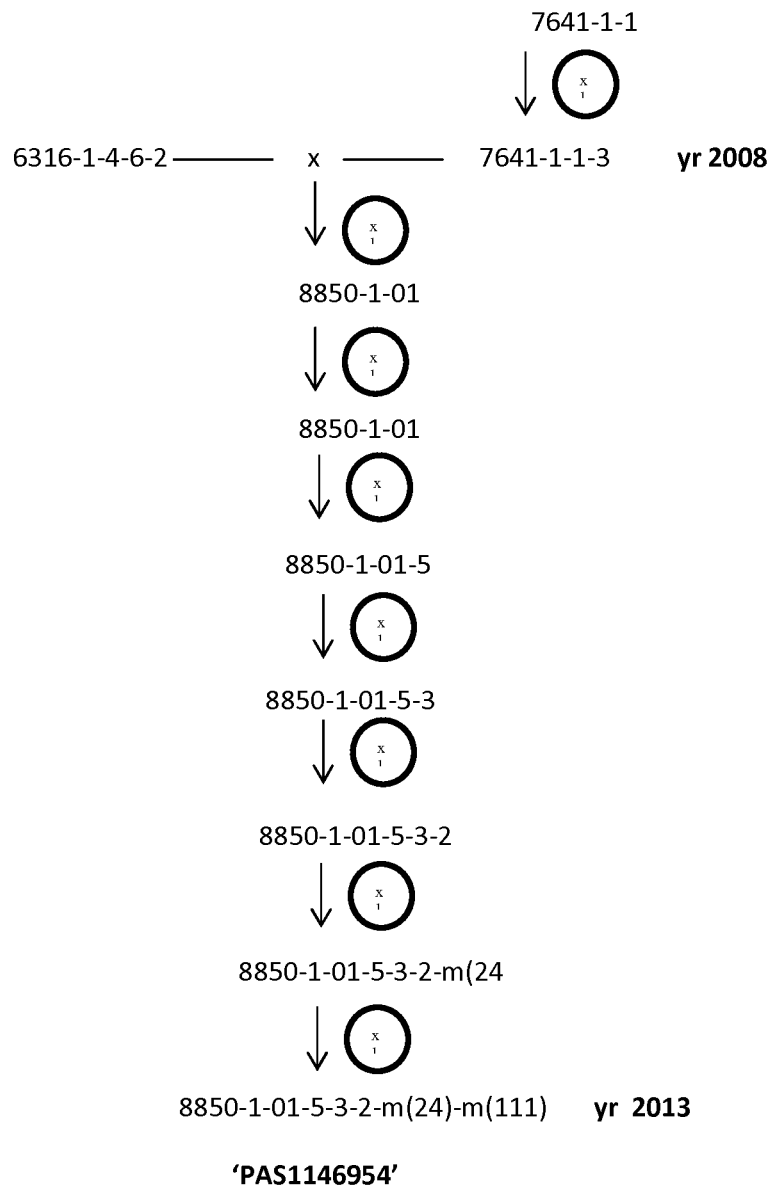

Breeding of the mutant lines resulted in the identification of *Tagetes* plants having unique phenotypes, such as dark red pigments in the lower epidermal layers of the ray floret. One of these plants was designated *Tagetes* variety TAS1146954'. The origin and breeding history of proprietary *Tagetes* variety TAS1146954' is presented in FIG. 3.

Example 3

HPLC Screening of Wild-Type and Mutant *Tagetes patula* Whole Ray Florets

Wild-type and mutant plants of *Tagetes patula* were grown in greenhouses in Santa Paula, Calif. using standard practices known in the art. The ray florets from fully-opened inflorescences were collected for analysis. Ray florets were removed from the base of the inflorescences and lyophilized for at least 50 hours. Samples were then ground through 40 mesh screen and stored at −20° C. after purging with helium gas.

An extraction solution of 85% ethanol and 15% 1N HCl was added to each sample to yield a final concentration of 5 mg sample dry weight/ml extraction solution. Tissue was extracted in 20-ml clear scintillation vials on a vortex shaker at 10,000 rpm for 60 minutes. The extract was filtered through a 0.45µ filter, and 10 µl of the solution was injected directly into the HPLC for analysis.

HPLC analysis was carried out on a Waters Alliance system 2690 with PDA detector. The column used was Zorbax SB-C18 (Agilent technologies) with dimension 4.6× 150 mm (3.5µ). The column temperature was maintained at 26° C. The chromatogram was collected under gradient conditions with two mobile phases, A (0.1% Trifluoro acetic acid) and B (Water:Acetonitrile:Acetic acid:TFA; 50.4:48.5: 1:0.1). The initial mobile phase was A:B, 80:20. The ratio was changed to 40:60 in 26 minutes and maintained in that proportion for another 19 minutes. The mobile phase was brought back to the initial conditions in next 10 minutes. The acquired PDA data was extracted at 525 nm for anthocyanin analysis.

Identification of the anthocyanins was made by dereplication analysis, a comparison of retention times of the HPLC standard and the peak of interest, with cyanidin-3-glucoside (ChromaDex, Part No: 00011605), cyanidin-3-rutinoside (ChromaDex, Part No: 00011325), and the mass spectral analysis. The peaks in the chromatogram were identified by their molecular weight obtained from HPLC-MS. The previously described HPLC protocol was followed and MS identification was made by Intertek American Analytical Chemistry Laboratories (AAC), Champaign, Ill.

Quantification of cyanidin-3-glucoside (retention time, 13.21 min, SD, 0.06), cyanidin-3-rutinoside (retention time, 11.05 min, SD, 0.05), petunidin-3-glucoside (retention time, 15.53 min, SD, 0.06), and free cyanidin (retention time, 20.7 min, SD, 0.07) were all based on the standard cyanidin-3-glucoside (ChromaDex, Part No: 00011605). A 1-mg quantity of the standard was dissolved in 3 ml of 85% ethanol and 15% 1N HCl. After filtering thorough 0.45µ PTFE filter, 10 µL of the sample were injected for the HPLC analysis. The average area under the HPLC chromatogram at 525 nm for cyanidin-3-glucoside for three injections was used to calculate the area corresponding to 1 µg of the standard. Wild-type and mutant samples were run in triplicate. From the area obtained for the standard, corresponding to 1 µg, and the average area obtained for wild-type and mutant from triplicate analysis for each peak, the amounts of cyanidin-3-glucoside, cyanidin-3-rutinoside, petunidin-3-glucoside, and free cyanidin were calculated in micrograms.

As shown in Table 1 below, the anthocyanin profiles of whole ray florets from mutant *Tagetes patula* plants was not distinct from those of all wild-type plants. All prdr1-1 mutant selections are identified with the letters MT.

TABLE 1

Anthocyanin content of whole ray florets of wild-type and mutant *Tagetes patula*

| Cultivar/Selection | Cyanidin-3-rutinoside (µg/g dw) | Cyanidin-3-glucoside (µg/g dw) | Petunidin-3-glucoside (µg/g dw) | Cyanidin (µg/g dw) | Total Anthocyanin (µg/g dw) | % Petunidin-3-glucoside |
|---|---|---|---|---|---|---|
| Durango Gold | 0 | 0 | 0 | 0 | 0 | 0 |
| Hero Harmony | 3111.1 | 1425.6 | 29.6 | 197.2 | 4763.5 | 0.6 |
| Bonanza Harmony | 4319.7 | 564.2 | 31.5 | 348.0 | 5263.3 | 0.6 |
| MT35423* | 4580.6 | 5193.7 | 113.6 | 858.9 | 10746.8 | 1.1 |
| MT35429 | 4071.0 | 1276.7 | 128.2 | 283.7 | 5759.6 | 2.2 |
| MT35440 | 9254.4 | 2159.0 | 141.0 | 304.4 | 11858.8 | 1.2 |

*MT35423 corresponds to Tagetes variety 'PAS1146954'.

Example 4

HPLC Screening of Ray Floret Lower Epidermal Layers of Wild-Type and Mutant *Tagetes patula*

Wild-type and mutant plants of *Tagetes patula* were grown as described in Example 3. The ray florets from fully-opened inflorescences were collected for analysis. The lower epidermal layers of the ray florets were peeled away from the upper layers using a steel spatula. The lower layers were then rinsed gently with double distilled water and air dried on paper towels. The air-dried tissue was then lyophilized for at least 50 hours. Samples were then ground through 40 mesh screen and stored at −20° C. after purging with helium gas. Extraction and sample analysis was performed as described in Example 3.

In Table 2 below, all prdr1-1 mutant selections are identified with the letters MT. Wild type selections include commercially available varieties, as well as an experimental selection from Ball Horticultural Company. The analysis illustrates that petunidin-3-glucoside is only observed in the lower epidermal layers of prdr1-1 mutant selections.

Wild type cultivars were chosen to cover the ranges of commercially known phenotypes of yellow, gold, orange, and maroon or mahogany patterns. To observe the mutant allele in the same genetic background, four mutant selections were backcrossed to the cultivar 'Little Devil Fire' or selections of it. The final phenotypes included ranges of dark to light red and a golden yellow tipped with maroon. In comparison, the wild type Hot Pak cultivars and the BHC Experimental Yellow are backcrosses to 'Little Devil Fire' or selections of it. The results in Table 2 below illustrate that petunidin-3-glucoside is present in the lower epidermal layers all backcrossed mutant selections, MT35437, MT35439, MT35442, and MT35447, and not detected in the lower epidermal layers of the wild type Hot Pak cultivars and 'Little Devil Fire'. For the wild-type comparisons, at least one representative of each known *Tagetes patula* color type was selected.

TABLE 2

Anthocyanin content of ray floret lower epidermal layers of wild-type and mutant *Tagetes patula*

| Cultivar/Selection | Cyanidin-3-rutinoside (μg/g dw) | Cyanidin-3-glucoside (μg/g dw) | Petunidin-3-glucoside (μg/g dw) | Cyanidin (μg/g dw) | Total Anthocyanin (μg/g dw) | % Petunidin-3-glucoside |
|---|---|---|---|---|---|---|
| Durango Bolero | 50.2 +/− 9.5 | 0 | 0 | 0 | 50.2 | 0 |
| Durango Gold | 0 | 0 | 0 | 0 | 0 | 0 |
| Safari Red | 774.5 +/− 4.4 | 66.9 +/− 17.7 | 0 | 45.5 +/− 12.7 | 887.0 | 0 |
| Bonanza Deep Orange | 0 | 0 | 0 | 0 | 0 | 0 |
| Bonanza Bee | 186.2 +/− 14.0 | 0 | 0 | 0 | 186.2 | 0 |
| Bonanza Yellow | 0 | 0 | 0 | 0 | 0 | 0 |
| Bonanza Orange | 0 | 0 | 0 | 0 | 0 | 0 |
| Cresta Flame | 461.9 +/− 5.2 | 66.9 +/− 9.2 | 0 | 62.0 +/− 8.5 | 590.8 | 0 |
| Hero Harmony | 854.7 +/− 26.3 | 124.7 +/− 23.5 | 0 | 69.0 +/− 6.8 | 1048.4 | 0 |
| Exp. Yellow - BHC | 0 | 0 | 0 | 0 | 0 | 0 |
| Hot Pak Gold | 0 | 0 | 0 | 0 | 0 | 0 |
| Hot Pak Orange | 0 | 0 | 0 | 0 | 0 | 0 |
| Hot Pak Flame | 334.2 +/− 44.3 | 0 | 0 | 0 | 334.2 | 0 |
| Hot Pak Harmony | 437.5 +/− 51.9 | 66.6 +/− 7.9 | 0 | 0 | 504.1 | 0 |
| Little Devil Fire | 74.0 +/− 11.0 | 0 | 0 | 0 | 74.0 | 0 |
| Bonanza Harmony | 530.0 +/− 63.9 | 122.0 +/− 16.2 | 0 | 0 | 652.0 | 0 |
| MT35420 | 8620.6 +/− 39.1 | 637.0 +/− 34.0 | 91.9 +/− 12.8 | 48.3 +/− 13.6 | 9397.8 | 1.0 |
| MT35423* | 5953.2 +/− 111.8 | 4884.4 +/− 32.9 | 216.5 +/− 3.8 | 283.1 +/− 18.4 | 11337.1 | 2.0 |
| MT35426 | 4665.6 +/− 23.4 | 4487.8 +/− 103.6 | 239.7 +/− 7.6 | 842.6 +/− 18.9 | 10235.7 | 2.3 |
| MT35427 | 8697.2 +/− 82.9 | 3143.2 +/− 113.7 | 247.3 +/− 8.8 | 764.7 +/− 30.0 | 12852.5 | 1.9 |
| MT35429 | 10046.6 +/− 51.9 | 3373.8 +/− 15.5 | 307.4 +/− 12.1 | 43.6 +/− 13.3 | 13771.3 | 2.2 |
| MT35437 | 5262.9 +/− 128.0 | 1889.8 +/− 5.0 | 100.5 +/− 11.5 | 245.6 +/− 15.7 | 7498.7 | 1.3 |
| MT35439 | 6766.4 +/− 40.0 | 531.8 +/− 17.0 | 60.3 +/− 9.9 | 46.3 +/− 2.0 | 7404.8 | 0.8 |
| MT35440 | 8886.8 +/− 110.2 | 882.5 +/− 21.2 | 153.5 +/− 6.1 | 133.2 +/− 4.3 | 10056.0 | 1.5 |
| MT35442 | 3423.0 +/− 55.2 | 879.2 +/− 40.0 | 70.6 +/− 5.8 | 257.0 +/− 1.0 | 4629.8 | 1.5 |
| MT35445 | 4582.9 +/− 55.6 | 799.7 +/− 26.1 | 136.6 +/− 9.3 | 399.4 +/− 4.8 | 5918.5 | 2.3 |
| MT35446 | 3239.8 +/− 31.0 | 279.4 +/− 33.2 | 87.7 +/− 12.3 | 184.4 +/− 13.4 | 3791.4 | 2.3 |
| MT35447 | 1898.2 +/− 3.8 | 89.2 +/− 9.2 | 24.5 +/− 2.6 | 80.7 +/− 8.3 | 2100.8 | 1.2 |

*MT35423 corresponds to Tagetes variety 'PAS1146954'.

Example 5

HPLC Screening of Ray Floret Lower Epidermal Layers of Wild-Type Marigold Plants and Mutant Triploid Marigold

*Tagetes patula* plants were used as a male parent plant and crossed with a *Tagetes erecta* plant as a female parent plant to obtain triploid (3N) marigold progeny seeds. Seeds were planted and grown to produce sterile triploid progeny plants, which were grown in greenhouses in Santa Paula, Calif. using standard practices known in the art. The ray florets from fully-opened inflorescences were collected for analysis and the lower epidermal layers of the ray florets were processed as described in Example 4. Extraction and sample analysis was performed as described in Example 3.

In Table 3 below, prdr1-1 triploid mutant selections are identified as MT60710, MT60711, and MT60724. Durango Red is a wild-type commercially available *Tagetes patula* variety. WT60692 is a wild-type triploid marigold created from a cross of a Ball Horticultural Company proprietary *Tagetes erecta* breeding selection coded 44030-2 as the female parent and Durango Red as the male parent. All triploid marigolds for this analysis were created using *Tagetes erecta* breeding selection coded 44030-2 as the female parent. MT60709 is a mutant *Tagetes patula* selection of the present invention, and is the male parent of triploid mutant selection MT60710. Different mutant *Tagetes patula* selections of the present invention were used as male parents to create the triploid mutant selections MT60711 and MT60724. The analysis illustrates that petunidin-3-glucoside is only observed in the lower epidermal layers of the prdr1-1 mutant *Tagetes patula* male parent and mutant triploid selections MT60710, MT60711, and MT60724.

TABLE 3

Anthocyanin content of ray floret lower epidermal layers of mutant triploid marigold

| Cultivar/Selection | Cyanidin-3-rutinoside (μg/g dw) | Cyanidin-3-glucoside (μg/g dw) | Petunidin-3-glucoside (μg/g dw) | Cyanidin (μg/g dw) | Total Anthocyanin (μg/g dw) | % Petunidin-3-glucoside |
|---|---|---|---|---|---|---|
| Durango Red *T. patula* | 815.2 +/− 31.7 | 151.2 +/− 15.3 | 0 | 0 | 966.4 | 0 |
| WT60692 triploid | 0 | 0 | 0 | 0 | 0 | 0 |
| MT60709 *T. patula* | 9536.2 +/− 110.2 | 2555.5 +/− 63.2 | 279.3 +/− 8.0 | 342.0 +/− 16.3 | 12712.9 | 2.2 |
| MT60710* | 3027.2 +/− 8.6 | 195.1 +/− 46.0 | 86.9 +/− 12.1 | 47.8 +/− 3.5 | 3357.1 | 2.6 |
| MT60711* | 4548.9 +/− 1.8 | 281.7 +/− 11.5 | 125.6 +/− 12.8 | 54.8 +/− 13.0 | 5011.1 | 2.5 |
| MT60724* | 3961.6 +/− 44.9 | 246.3 +/− 47.4 | 127.3 +/− 17.8 | 13.5 +/− 9.8 | 4348.7 | 2.9 |

*Indicates prdr1-1 triploid mutant selections

What is claimed is:

1. A *Tagetes patula* ray floret comprising cyanidin-3-rutinoside, cyanidin-3-glucoside, petunidin-3-glucoside, and cyanidin in the lower epidermal layers of the ray floret, wherein the ray floret comprises a prdr1-1 allele that confers petunidin-3-glucoside in the lower epidermal layers of the ray floret, and wherein a representative deposit of seed comprising the prdr1-1 allele has been deposited under ATCC Accession No. PTA-121614.

2. The ray floret of claim 1, wherein said prdr1-1 allele further confers a red color in the lower epidermal layers of the ray floret.

3. A plant comprising the ray floret of claim 1.

4. A seed that produces the plant of claim 3.

5. The ray floret of claim 1, further comprising a transgene.

6. The ray floret of claim 1, wherein the ray floret comprises a single locus conversion.

7. A method of introducing a desired trait into a plant comprising:
(a) crossing a first plant according to claim 3 with a second plant that comprises a desired trait to produce F1 progeny;
(b) selecting an F1 progeny that comprises the desired trait;
(c) crossing the selected F1 progeny with a plant of the same variety as said first plant to produce backcross progeny; and
(d) repeating steps (c) and (d) three or more times in succession to produce selected fourth or higher backcross progeny that comprise the desired trait.

8. A plant produced by the method of claim 7, wherein the plant comprises said prdr1-1 allele.

9. A method for producing *Tagetes* seed comprising the steps of:
(a) crossing a first plant according to claim 3 with itself or a second plant capable of being crossed thereto; and
(b) collecting resulting seed.

10. The method of claim 9, further comprising the steps of:
(c) crossing a plant grown from said seed of step (b) with itself or a different plant at least one additional time to yield additional seed.

11. The method of claim 9, wherein the second plant is a *Tagetes erecta* plant.

12. The method of claim 9, wherein the first plant is a plant of *Tagetes* variety 'PAS1146954', a sample of seed of said *Tagetes* variety having been deposited under ATCC Accession Number PTA-121614.

* * * * *